US008466080B2

(12) United States Patent
Boldingh

(10) Patent No.: US 8,466,080 B2
(45) Date of Patent: Jun. 18, 2013

(54) CATALYSTS, PROCESSES FOR PREPARING THE CATALYSTS, AND PROCESSES FOR TRANSALKYLATING AROMATIC HYDROCARBON COMPOUNDS

(75) Inventor: Edwin P. Boldingh, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 195 days.

(21) Appl. No.: 12/882,400

(22) Filed: Sep. 15, 2010

(65) Prior Publication Data

US 2012/0065446 A1   Mar. 15, 2012

(51) Int. Cl.
*B01J 29/06* (2006.01)

(52) U.S. Cl.
USPC ............... 502/67; 502/63; 502/64; 502/66; 502/71; 502/78

(58) Field of Classification Search
USPC .................. 502/63, 64, 66, 67, 71, 78
See application file for complete search history.

(56) References Cited

U.S. PATENT DOCUMENTS

| 3,898,297 | A |   | 8/1975 | Sampson et al. | |
|---|---|---|---|---|---|
| 4,709,110 | A |   | 11/1987 | Rodewald | |
| 4,939,110 | A | * | 7/1990 | Sachtler et al. | 502/66 |
| 5,106,801 | A | * | 4/1992 | Zones et al. | 502/64 |
| 5,254,514 | A | * | 10/1993 | Nakagawa | 502/62 |
| 5,344,997 | A |   | 9/1994 | Kocal | |
| 5,600,050 | A |   | 2/1997 | Huang et al. | |
| 5,990,031 | A |   | 11/1999 | Ghosh | |
| 6,166,281 | A |   | 12/2000 | Anantaneni | |
| 7,220,885 | B2 | * | 5/2007 | Boldingh et al. | 585/475 |
| 7,314,601 | B2 |   | 1/2008 | Negiz et al. | |
| 7,381,677 | B1 | * | 6/2008 | Bogdan et al. | 502/64 |
| 7,393,805 | B2 |   | 7/2008 | Boldingh et al. | |
| 7,446,069 | B2 |   | 11/2008 | Ghosh et al. | |
| 7,456,124 | B2 |   | 11/2008 | Boldingh et al. | |
| 7,544,849 | B2 |   | 6/2009 | Boldingh et al. | |
| 7,566,810 | B2 |   | 7/2009 | Boldingh et al. | |
| 7,615,197 | B2 |   | 11/2009 | Negiz et al. | |
| 7,626,064 | B1 | * | 12/2009 | Boldingh et al. | 585/475 |
| 2002/0082460 | A1 | * | 6/2002 | Verduijn et al. | 585/475 |
| 2005/0202955 | A1 | * | 9/2005 | McMinn et al. | 502/64 |
| 2006/0189477 | A1 |   | 8/2006 | Ghosh | |
| 2007/0167660 | A1 | * | 7/2007 | Guillon et al. | 585/481 |
| 2008/0064588 | A1 |   | 3/2008 | Boldingh | |
| 2009/0023967 | A1 |   | 1/2009 | Sohn et al. | |
| 2009/0036724 | A1 | * | 2/2009 | Negiz et al. | 585/470 |
| 2009/0093661 | A1 | * | 4/2009 | Guillon et al. | 585/477 |
| 2009/0099007 | A1 |   | 4/2009 | Khare | |
| 2009/0156871 | A1 | * | 6/2009 | Khare | 585/408 |
| 2009/0299115 | A1 | * | 12/2009 | Guillon et al. | 585/481 |
| 2009/0325785 | A1 |   | 12/2009 | Moscoso et al. | |

FOREIGN PATENT DOCUMENTS

EP          0337273 A2    10/1999

* cited by examiner

*Primary Examiner* — Elizabeth Wood
(74) *Attorney, Agent, or Firm* — Mark R Willis

(57) ABSTRACT

A catalyst comprising an aluminosilicate zeolite having an MOR framework type, an acidic MFI molecular sieve component having a $Si/Al_2$ molar ratio of less than 80, a metal component comprising one or more elements selected from groups VIB, VIIB, VIII, and IVA, an inorganic oxide binder, and a fluoride component.

10 Claims, 1 Drawing Sheet

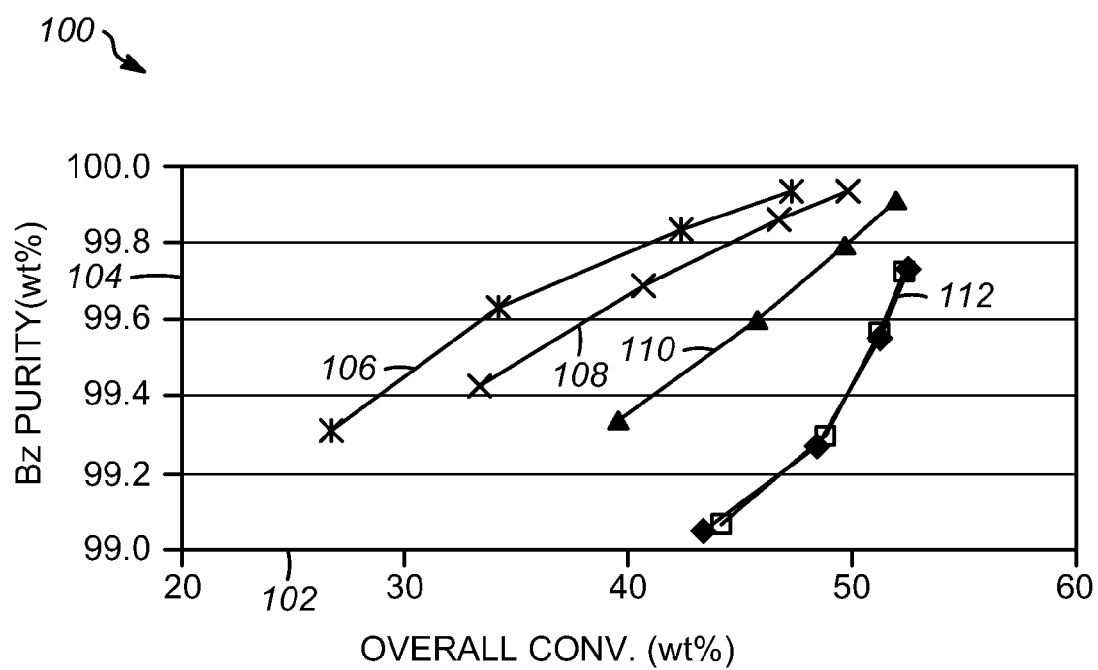

CATALYSTS, PROCESSES FOR PREPARING THE CATALYSTS, AND PROCESSES FOR TRANSALKYLATING AROMATIC HYDROCARBON COMPOUNDS

FIELD OF THE INVENTION

The present invention generally relates to improved catalysts, and more particularly relates to catalysts and processes for transalkylating aromatic hydrocarbon compounds.

DESCRIPTION OF RELATED ART

Xylene isomers ("xylenes") and benzene are produced in large volumes from petroleum by the reforming of naphtha. However, neither the xylenes nor benzene are produced in sufficient volume to meet demand. Consequently, other hydrocarbons are necessarily converted to increase the yield of the xylenes and benzene via processes such as transalkylation, disproportionation, isomerization, and dealkylation. For example, toluene commonly is dealkylated to produce benzene. Alternatively, or additionally, toluene can be disproportionated to yield benzene and C8 aromatics from which the individual xylene isomers are recovered.

More recently, development has been directed at selectively transalkylating heavier aromatics, such as C9+ aromatics, to increase the yield of xylenes and benzene from aromatics complexes. In this regard, a variety of catalysts have been developed for these processes. For example, a wide range of zeolites, including mordenite, have been disclosed as effective transalkylation catalysts. Shaped catalysts, multiple zeolites, metal modifiers, and treatments such as steam calcination have been described as increasing the effectiveness of the catalysts.

Although known catalysts are effective for producing xylenes and benzene, there is a need to improve catalyst stability and the ability of the catalysts to convert heavy feeds to desired products. Specifically, catalysts having a strong metal function are suitable to provide improved catalyst stability in a transalkylation process. However, in transalkylation processes employing such catalysts, aromatic rings may become saturated or even cleaved resulting in naphthene and acyclic paraffin (non-aromatics) co-production, which can result in a loss of valuable aromatics. Also, because some of the non-aromatics have similar boiling points to benzene (benzene co-boilers), they are not readily removed to achieve a benzene product having a desired purity for commercial applications (e.g., a purity of 99.85% or more). Although the benzene co-boilers can be fractionated or extracted with a solvent, such processes are expensive and typically require additional equipment.

Accordingly, it is desirable to provide a catalyst having improved stability during transalkylation processing of heavy feedstocks. In addition, it is desirable to provide a stable catalyst that can be used to provide benzene products having a high purity (e.g., a purity of 99.85% or more). Furthermore, other desirable features and characteristics of the present invention will become apparent from the subsequent detailed description of the invention and the appended claims, taken in conjunction with the accompanying drawing and this background of the invention.

SUMMARY OF THE INVENTION

In accordance with an embodiment, by way of example only, a catalyst includes an aluminosilicate zeolite having an MOR framework type, an acidic MFI molecular sieve component having a $Si/Al_2$ molar ratio of less than 80, a metal component comprising one or more elements selected from groups VIIB, VIIB, VIII, and IVA, an inorganic oxide binder, and a fluoride component.

In accordance with another embodiment, by way of example only, a process for transalkylating aromatics includes contacting a feed stream comprising aromatic compounds with a catalyst under transalkylation conditions, wherein the catalyst comprises an aluminosilicate zeolite having an MOR framework type, an acidic MFI molecular sieve component having a $Si/Al_2$ molar ratio of less than 80, a metal component comprising one or more elements selected from groups VIIB, VIIB, VIII, and IVA, an inorganic oxide binder, and a fluoride component.

In accordance with still another embodiment, by way of example only, a process for preparing a catalyst includes fluoriding a catalyst comprising a mordenite component, an acidic MFI molecular sieve component having a $Si/Al_2$ molar ratio of less than 80, a metal component comprising one or more elements selected from groups VIIB, VIIB, VIII, and IVA, and an inorganic oxide binder to form a fluorided catalyst.

BRIEF DESCRIPTION OF THE DRAWING

The present invention will hereinafter be described in conjunction with the following drawing FIGURE, wherein like numerals denote like elements, and wherein:

FIG. 1 is a graph illustrating the purity of benzene as a function of the weight percent of overall conversion of feedstock for various samples.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The various embodiments of the present invention are directed to a catalyst for use in aromatics transalkylation that is capable of forming benzene having purity that is improved over benzene produced when using conventional high-stability catalysts. The improved catalyst includes an aluminosilicate zeolite having an MOR framework type, an additional molecular sieve component, one or more metal components, an inorganic oxide binder, and a fluoride component. In another embodiment, the catalyst further comprises a sulfide component.

The aluminosilicate zeolite having an MOR framework is described in Atlas of Zeolite Framework Types, 6th Revised Edition, C. H. Baerlocher, L. B. McCusker, and D. H. Olson, editors, Elsevier (2007), pp. 218-219. The MOR framework comprises four- and five-membered rings of $SiO_4$ and $AlO_4$ tetrahedra to form a crystal lattice comprising 12-ring channels running parallel along a crystal axis to give a tubular configuration.

In an embodiment of the present invention, the aluminosilicate zeolite component having the MOR framework comprises UZM-14. UZM-14 is described in U.S. Pat. No. 7,626,064, which is incorporated herein by reference. UZM-14 generally has a silica-alumina mole ratio of from about 10 to about 50 and includes (1) globular aggregates have a mesopore volume of at least about 0.10 cc/gram, and preferably at least about 0.13 cc/gram;

(2) the UZM-14 crystallites have at least about $1 \times 10^{19}$ 12-ring channels/gram of UZM-14 material;
(3) the mean crystallite length parallel to the direction of the 12-ring channels is about 60 nm or less and preferably about 50 nm or less;
(4) The Si/Al2 ratio of the UZM-14 aggregate material generally is between about 8 and about 50, and preferably no more than about 30.

The UZM-14 has an empirical composition in the as-synthesized form on an anhydrous basis expressed by the empirical formula:

$$M_m^{n+}R_r^{p+}Al_{1-x}Si_yO_z$$

Where:
M is at least one exchangeable cation and is selected from the group consisting of alkali and alkaline earth metals including but not limited to lithium, sodium, potassium, rubidium, cesium, calcium, strontium, barium and mixtures thereof,
R is at least one organic cation selected from the group consisting of protonated amines, protonated diamines, quaternary ammonium ions, diquaternary ammonium ions, protonated alkanolamines, and quaternized alkanolammonium ions,
m is the mole ratio of M to Al and varies from about 0.05 to about 0.95
r is the mole ratio of R to Al and has a value of about 0.05 to about 0.95
n is the weighted average valence of M and has a value of about 1 to about 2
p is the weighted average valence of R and has a value of about 1 to about 2
y is the mole ratio of Si to Al and varies from about 3 to about 50
z is the mole ratio of O to Al and has a value determined by the equation:

$$z=(mn+rp+3+4y)/2$$

The additional molecular sieve component preferably is selected from one or more of MFI, MEL, EUO, FER, MFS, MTT, MTW, MWW, MAZ, TON and FAU (IUPAC Commission on Zeolite Nomenclature) and UZM-8 (see WO 2005/113439, incorporated herein by reference thereto). In an embodiment of the present invention, particularly when the catalyst is used in a transalkylation process, the additional molecular sieve component comprises a zeolite having an MFI type framework as described in *Atlas of Zeolite Framework Types*, 6th Revised Edition, C. H. Baerlocher, L. B. McCusker, and D. H. Olson, editors, Elsevier (2007). MFI type zeolites have a 3-dimensional 10-ring channel system: [100] 10-MR 5.1×5.5 Å and [010] 10-MR 5.3×5.6 Å.

The MFI molecular sieve is acidic and has a "Total Acidity" of at least about 0.15, preferably at least about 0.25, and most preferably at least about 0.4, for example, 0.4 to 0.8. Total Acidity is determined by Ammonia Temperature Programmed Desorption (Ammonia TPD). The Total Acidity of the MFI molecular sieve may be that of the MFI to be used in making the catalyst of the invention or may be achieved during the preparation of the catalyst. Typically, the MFI molecular sieve is at least partially in the hydrogen form in the finished catalyst. The Ammonia TPD process involves first heating a sample (about 250 milligrams) of molecular sieve at a rate of about 5° C. per minute to a temperature of about 550° C. in the presence of a 20 volume percent oxygen in helium atmosphere (flow rate of about 100 milliliters per minute). After a hold of about one hour, helium is used to flush the system (about 15 minutes) and the sample is cooled to about 150° C. The sample is then saturated with pulses of ammonia in helium at about 40 milliliters per minute. The total amount of ammonia used is greatly in excess of the amount required to saturate all the acid sites on the sample. The sample is purged with helium (about 40 milliliters per minute) for about 8 hours to remove physisorbed ammonia. With the helium purge continuing, the temperature is increased at a rate of about 10° C. per minute to a final temperature of 600° C. The amount of ammonia desorbed is monitored using a calibrated thermal conductivity detector. The total amount of ammonia is found by integration. Dividing the total amount of ammonia by the dry weight of the sample yields the Total Acidity. As used herein, values of Total Acidity are given in units of millimoles of ammonia per gram of dry sample. The unique combination of structure, channel system, acidity and stability makes MFI suitable as a secondary zeolite in aromatic transalkylation catalysts where one of its functions is too reduce the benzene co-boilers by cracking.

MFI molecular sieves used in the catalysts of this invention have a $Si/Al_2$ molar ratio of less than about 80, preferably less than about 40, more preferably less than about 25, for example, between about 15:1 to about 25:1. An example of a suitable MFI molecular sieve for inclusion in the catalyst includes, but is not limited to, ZSM-5 (which is disclosed in U.S. Pat. No. 3,702,886, incorporated herein, by reference). Another suitable MFI molecular sieve includes an MFI zeolite available from UOP, LLC of Des Plaines, Ill., an MFI molecular sieve available from Zeolyst International of Conschocken, Pa. or and/or an MFI molecular sieve available from Tosoh Corporation of Tokyo, Japan.

The inorganic-oxide binder component of the invention comprises such materials as alumina, silica, zirconia, titania, thoria, boria, magnesia, chromia, stannic oxide, and the like as well as combinations and composites thereof, for example silica-alumina, alumina-zirconia, alumina-titania, aluminum phosphate, and the like. Alumina is an especially preferred refractory inorganic oxide for use herein, particularly with respect to the manufacture of a catalytic composite for use in the transalkylation of alkylaromatic hydrocarbons. The alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like, the first mentioned alpha-alumina monohydrate being preferred. An alternative binder is aluminum phosphate.

The weight ratio of the MFI molecular sieve component to the aluminosilicate zeolite having the MOR framework is in the range of about 1:10 to 5:1, most preferably about 1:10 to 2:1. In an embodiment of the present invention, the aluminosilicate zeolite having the MOR framework comprises between about 20 to about 80 weight percent (wt. %) of the catalyst, the MFI molecular sieve component comprises between about 10 and about 70 wt. % of the catalyst, and the inorganic oxide binder comprises between about 1 and about 40 wt. % of the catalyst.

The metal component comprises one or more elements selected from groups VIB(6), VIIB(7), VIII(8-10), IB(11), IIB(12), IIIA(13) and IVA(14) of the Periodic Table. Preferably, the metal component is selected from one or more of rhenium, nickel, cobalt, molybdenum, tungsten, platinum, and palladium when the catalyst is used in a transalkylation process. In an embodiment in which rhenium is included, the rhenium may be present in the catalyst composite as a compound such as an oxide or sulfide, in chemical combination with one or more of the other ingredients of the composite. The catalyst may optionally additionally or alternatively contain other modifier metal components. Preferred metal modifier components of the catalyst include, for example, tin, germanium, lead, indium, and mixtures thereof. The metal components may be incorporated into the catalyst by any means known in the art, such as (co-)precipitation, ion-exchange, co-mulling or impregnation. A preferred amount is a range of about 0.01 to about 10.0 wt. % based upon the total weight of the catalyst. While not wishing to be limited by theory, catalytically effective amounts are those of mordenite for transalkylation, of acidic MFI zeolite for cracking benzene co-boilers (such as naphthenes), and of rhenium for enhancing overall conversion and catalyst stability at the selected process conditions.

The fluoride component is included to increase the acid strength of the hydroxyls on the catalyst. As a result, the fluorided catalyst allows more complete cracking of benzene co-boilers. The catalyst includes from about 1 wt. % to about 5 wt. % fluoride on an elemental basis. In a preferred embodiment, the catalyst includes from about 1 wt. % to about 2 wt. % fluoride on an elemental basis.

The catalyst also preferably includes from about 0.05 wt. % to about 3 wt. % sulfur on an elemental basis. Sulfur is employed as a modifier and is included to attenuate the metal function of the catalyst. Specifically, inclusion of the sulfur reduces saturation of the aromatic ring compounds in the feedstock.

The catalyst can be formed by combining the aluminosilicate zeolite having the MOR framework, the MFI molecular sieve component, and the inorganic oxide binder in any conventional or otherwise convenient manner to form spheres, pills, pellets, granules, extrudates, or other suitable particle shape. For example, finely divided aluminosilicate zeolite having the MOR framework and MFI molecular sieve particles, and metal salt particles can be dispersed in an alumina sol, and the mixture in turn dispersed as droplets in a hot oil bath whereby gelation occurs with the formation of spheroidal gel particles. A preferred method comprises comingling a finely divided form of the selected aluminosilicate zeolite having the MOR framework and MFI molecular sieve particles, a refractory inorganic oxide, and a metal salt with an inorganic oxide binder and/or lubricant and compressing the mixture into pills or pellets of uniform size and shape. Alternatively, and still more preferably, the aluminosilicate zeolite having the MOR framework and MFI molecular sieve particles, refractory inorganic oxide, and metal salt are combined and admixed with a peptizing agent in a mix-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobates, with a trilobe form being favored. The extrudates also may be formed into spheres by means of a spinning disc or drum and then dried and calcined.

Subsequently, the extrudates can be impregnated with a soluble, decomposable compound containing the metal component to form a composite. In embodiments in which rhenium is the metal component, typical compounds which may be employed include ammonium perrhenate, sodium perrhenate, potassium perrhenate, potassium rhenium oxychloride, potassium hexachlororhenate (IV), rhenium chloride, perrhenic acid, and the like compounds. Preferably, the compound is ammonium perrhenate or perrhenic acid because no extra steps may be needed to remove any co-contaminant species. In other embodiments in which the desired metal component comprises molybdenum, typical compounds which may be employed include, ammonium heptamolybdate, alkali metal molybdates (also peroxo-, di-, tri-, tetra-, hepta-, octa-, or tetradecamolybdate), molybdic acid, phosphomolybdic acid, Mo—P heteropolyanion compounds, acetyl acetonates, Mo(0) metal, Mo oxides, Mo peroxo complexes, and mixtures thereof. The composite is preferably calcined in an air atmosphere at a temperature of from about 425° to about 750° C., preferably at a temperature of from about 475° to about 600° C., over a period of from about 0.5 to about 10 hours.

Next, the composite is subjected to a fluoriding step to incorporate from about 0.1 wt. % to about 5.0 wt. % fluoride on an elemental basis. The fluoride component may be incorporated into the catalyst by any known technique. For example, incorporation can occur by impregnating the catalyst with essentially hydrogen fluoride (HF) or a fluoride source that is substantially equivalent to HF in affording a fluorided catalyst substantially free (e.g., at least 99% free) of additional metals or metallic species and which analytically contains only additional HF. Examples of a suitable fluoride sources, in addition to HF, include but are not limited to ammonium fluoride ($NH_4F$), ammonium bifluoride ($NH_4HF_2$), and organic fluorides. In an embodiment in which an ammonium fluoride is used $NH_3$ is volatilized during subsequent heating of the fluoride-impregnated catalyst. When organic fluorides are used the impregnated catalyst is subsequently heated under conditions which oxidize carbon to carbon dioxide and excess hydrogen to water, both of which volatilize to leave the equivalent of an HF-impregnated product.

The preparation of the fluorided catalyst may be performed by a variety of procedures, depending upon the fluoride source, fluoride level sought, and so forth. For example, when an ammonium fluoride is used, equal volumes of the catalyst base and an aqueous solution of the ammonium fluoride containing the desired amount of fluoride are intimately mixed, (e.g., cold rolled) and the mixture subsequently heated to evaporate the water. The resulting fluoride-impregnated product may be dried at about 125° C. to about 175° C. for several hours, and then calcined at a temperature typically in a range of about 350° C. to about 550° C. for 1-6 hours, depending on the temperature used. For calcination near 400° C., calcination occurs for about 3 hours.

In an embodiment in which HF is the fluoride source, an impregnation method similar to the aforementioned method may be used, although it also is possible to fluoride the catalyst with a gaseous HF stream. In the latter instance, no drying step is necessary and the fluorided material may be calcined directly. The catalyst may be impregnated using either a vapor phase or liquid phase source of fluoride when an organic fluoride is used. For example, an organic fluoride such as t-butyl fluoride can be impregnated from its solution in a volatile solvent, the solvent subsequently removed by evaporation, and then the catalyst heated to remove the last traces of solvent and then calcined to remove the organic material. Alternatively, the t-butyl fluoride may be volatilized, and HF deposited on the silica-alumina via thermal decomposition of the t-butyl fluoride. Fluoride levels can be controlled by gas rate, time and temperature of exposure.

In an embodiment, the fluoride treatment is initiated by incorporating a source of fluoride into the feed and continuing fluoride treatment for a time sufficient to provide the sought amount of fluoriding. Depending upon the concentration of the fluoride in the feed, fluoriding can be completed in less than one hour or may be completed over a longer period of time, e.g., for a day or more. The fluoride treatment may be monitored by measuring the concentration of fluoride in the product off gas. The time calculated for fluoride treatment will depend on the actual concentration of fluoride in the feed and the desired fluoride loading to be achieved on the catalyst.

To enhance catalyst selectivity, the composite can be further subjected to a sulfiding step to incorporate from about 0.05 to about 3 wt. % sulfur on an elemental basis. The sulfur component may be incorporated into the catalyst by any known technique. Any one or a combination of in situ and/or ex situ sulfur treatment methods is preferred. The resulting catalyst mole ratio of sulfur to rhenium is preferably from about 0.1 to less than about 1.5, and even more preferably the catalyst mole ratio of sulfur to rhenium is about 0.3 to about 0.8. The catalyst is treated with a source of sulfur at a temperature ranging from about 0° C. to about 500° C. directly or via a carrier gas, typically, hydrogen or an inert gas such as nitrogen. Alternatively, a source of sulfur is added to a hydrocarbon feed stream in a concentration ranging from about 1 ppm-mole sulfur to about 5,000 or 10,000, preferably from about 5 to 1000 ppm-mole sulfur. Typical examples of appropriate sources of sulfur include hydrogen sulfide, carbon disulfide and alkylsulfides such as methylsulfide, dimethylsulfide, dimethyldisulfide, diethylsulfide and dibutylsulfide. Sulfiding may be completed in less than one hour or may be completed over a longer period of time, e.g., for a day or more, depending on an actual concentration of sulfur in the feed and the desired sulfur loading to be achieved on the catalyst. The sulfiding step may take place either during the manufacture of the catalyst or after the catalyst has been loaded into a process unit.

The catalysts described above are useful for xylene isomerization, toluene disproportionation to xylenes and benzene, and transalkylation of aromatics with 9 or more carbon atoms with at least one of toluene and benzene to produce xylenes. The catalysts are attractive for converting ethylbenzene to benzene and the dealkylation of ethyl and higher alkyl groups of alkylbenzenes such as methyl ethyl benzene. The catalysts are also attractive for converting non-aromatics, for example, to saturate and/or crack non-aromatics. Feedstocks for xylene isomerization can contain ethylbenzene, for example, between about 5 and 60 mass percent, and ethylbenzene can be converted. Advantageously, when the above-described catalysts are used in the aforementioned reactions, the benzene produced by the reactions has an improved purity over reactions in which conventional catalysts are employed.

An aromatics-rich feed stream to a transalkylation or disproportionation process during which contact with the above-described catalysts will occur may be derived from a variety of sources, including without limitation catalytic reforming, pyrolysis of naphtha, distillates or other hydrocarbons to yield light olefins and heavier aromatics-rich byproducts, and catalytic or thermal cracking of heavy oils to yield products in the gasoline range. Products from pyrolysis or other cracking operations generally will be hydrotreated according to processes well known in the industry before being charged to the complex in order to remove sulfur, olefins and other compounds which would affect product quality. Light cycle oil also may be beneficially hydrocracked to yield lighter components which can be reformed catalytically to yield the aromatics-rich feed stream. If the feed stream is catalytic reformate, the reformer preferably is operated at high severity for high aromatics yield with a low concentration of nonaromatics in the product. The reformate also advantageously is subjected to olefin saturation to remove potential product contaminants and materials that could polymerize to heavy nonconvertibles in a transalkylation process. Such processing steps are described in U.S. Pat. No. 6,740,788 B1, incorporated herein by reference thereto.

Generally, a preferred component of the feedstock is a heavy-aromatics stream comprising C9+ aromatics, thereby effecting transalkylation of toluene and C9+ aromatics to yield additional xylenes. Benzene is also transalkylated to yield additional toluene. Indane may be present in the heavy-aromatics stream although it is not a desirable component to effect high yields of C8 aromatics product. C10+ aromatics also may be present, preferably in an amount of 30% or less of the feed. The heavy-aromatics stream preferably comprises at least about 90 mass % aromatics, and may be derived from the same or different known refinery and petrochemical processes as the benzene and toluene feedstock and/or may be recycled from the separation of the product from transalkylation.

In addition to the C9+ aromatics, the feedstream (e.g., a stream of material including feedstock) comprises alkylaromatic hydrocarbons of the general formula $C_6H_{(6-n)}R_n$, where n is an integer from 0 to 5 and R is $CH_3$, $C_2H_5$, $C_3H_7$, or $C_4H_9$, in any combination. Suitable alkylaromatic hydrocarbons include, for example but without so limiting the invention, benzene, toluene, ortho-xylene, meta-xylene, para-xylene, ethylbenzene, ethyltoluenes, propylbenzenes, tetramethylbenzenes, ethyl-dimethylbenzenes, diethylbenzenes, methylethylbenzenes, methylpropylbenzenes, ethylpropylbenzenes, triethylbenzenes, trimethybenzenes, diisopropylbenzenes, and mixtures thereof.

In embodiments in which a transalkylation or disproportionation process is performed, the feed stream can include a substantially pure alkylaromatic hydrocarbon of from about 6 to about 15 carbon atoms, a mixture of such alkylaromatic hydrocarbons, or a hydrocarbon fraction rich in said alkylaromatics. The feed stream also may comprise benzene and aromatics having from 2 to 4 rings. Suitable components of the feed stream thus generally include, for example but without so limiting the invention, benzene, toluene, ethylbenzene, meta-xylene, ortho-xylene, para-xylene, ethyl-toluenes, trimethylbenzenes, diethyl-benzenes, triethylbenzenes, propylbenzenes, methylpropylbenzenes, ethylpropylbenzenes, diisopropylbenzenes, butylbenzenes, indanes, naphthalenes, tetralins, decalins, biphenyls, diphenyls and fluorenes. The feed stream also may contain lesser concentrations of non-aromatics such as pentanes, hexanes, heptanes and heavier paraffins along with paraffins along with methylcyclopentane, cyclohexane and heavier naphthenes; pentanes and lighter paraffins generally will have been removed before processing in the aromatics complex. The combined transalkylation feed preferably contains no more than about 10 wt. % nonaromatics; olefins preferably are restricted to a Bromine Index of no more than about 1000, and preferably no more than about 500.

The feed to a transalkylation reaction zone is first heated by indirect heat exchange against the effluent of the reaction zone and then is heated to reaction temperature by exchange with a warmer stream, steam or a furnace. The feedstock is preferably transalkylated in the vapor phase and in the presence of hydrogen. If present, free hydrogen is associated with the feedstock and recycled hydrocarbons in an amount of from about 0.1 moles per mole of alkylaromatics up to 10 moles per mole of alkylaromatic. If transalkylated in the liquid phase, then the presence of hydrogen is optional. This ratio of hydrogen to alkylaromatic is also referred to as hydrogen to hydrocarbon ratio. The transalkylation reaction yields a product having xylene and toluene.

The feed then is passed through a reaction zone comprising one or more individual reactors to produce an effluent comprising unconverted feed and product hydrocarbons. This effluent is normally cooled by indirect heat exchange against the stream entering the reaction zone and then further cooled through the use of air or cooling water. The effluent may be passed into a stripping column in which substantially all C5 and lighter hydrocarbons present in the effluent are concentrated into an overhead stream and removed from the process. An aromatics-rich stream is recovered as net stripper bottoms, which is referred to herein as the transalkylation effluent.

Contact with the catalyst can be effected in any conventional or otherwise convenient manner and may occur as a batch or continuous type of operation. The catalyst is disposed as a fixed bed in a reaction zone of a vertical tubular reactor with the alkylaromatic feed stock charged through the bed in an upflow or downflow manner. The reaction can occur at a temperature in a range of from about 200° to about 540° C., preferably between about 200° to about 480° C., at a pressure in a range of from about 100 kPa to about 6 Mpa absolute, and over a range of space velocities, such as a liquid hourly space velocity (i.e., volume of charge per volume of catalyst per hour) in a range of from about 0.1 to about 20 $hr^{-1}$.

The transalkylation effluent is separated into a light recycle stream, a mixed C8 aromatics product, and a heavy-aromatics stream. The mixed C8 aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all of the C9 and heavier aromatics and may be partially or totally recycled to the transalkylation reaction zone.

Examples

The following are examples of the preparation and testing of a catalyst, in accordance with exemplary embodiments described herein. The examples are provided for illustration purposes only, and are not meant to limit the various embodiments of the present invention in any way.

Four samples were prepared and tested. A reference sample was made by blending a mixture of, by weight, 50% UZM-14 (nano mordenite) (available through UOP LLC of Des Plaines, Ill.) and 25% MFI zeolite (available through UOP LLC of Des Plaines, Ill.), and 25% peptized Catapal B (available through Vista Chemical Company of Houston, Tex.) were admixed with nitric acid (to peptize the alumina) and a solution of ammonium heptamolybdate to form a dough containing 3% molybdenum (on volatile-free basis). The dough was pressured through a die to form an extrudate that was calcined for two hours in air at 500° C. Samples A, B, and C were also prepared by blending a mixture of, by weight, 50% UZM-14 (nano mordenite) and 25% MFI zeolite, and 25% peptized Catapal B. The mixture was extruded and calcined for two hours in air at 500° C. The calcined extrudates were then impregnated with a solution of ammonium bifluoride ($NH_4HF_2$) and ammomium heptamolybdate to produce a finished catalyst with a target level of, by weight, 3% molybdenum and different target levels of fluorine (e.g., by weight, 1% for Sample A, 2% for Sample B, and 5% for Sample C). When analyzed, Sample A included 3.4 wt. % molybdenum and 1.0 wt. % fluorine, Sample B included 3.2 wt. % molybdenum and 1.9 wt. % fluorine, and Sample C included 2.8 wt. % molybdenum and 2.1 wt. % fluorine. Each of the samples were contacted with a feedstream comprising about 75 wt. % toluene and about 25 wt. % C9+ aromatic compounds.

FIG. 1 is a graph 100 illustrating the purity of benzene as a function of the weight percent of overall conversion of feedstock for the Reference Sample and Samples A-C as represented by lines 112, 110, 108, and 106, respectively. As shown in FIG. 1, x-axis 102 represents an overall conversion of the feedstock, by weight percent, and y-axis 104 represents benzene purity in terms of weight percent. Benzene purity was calculated by dividing a total yield of non-aromatics (e.g., C6-C7) in terms of weight percent by the total yield of benzene in terms of weight percent. As illustrated in FIG. 1, Sample C, represented by line 106 indicates that use of Sample C yields a higher benzene purity than use of Sample A (represented by line 108), Sample B (represented by line 110), and the Reference Sample (represented by line 112).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A catalyst comprising:
   an aluminosilicate zeolite having an MOR framework type;
   an acidic MFI molecular sieve component having a $Si/Al_2$ molar ratio of less than 80;
   a metal component comprising one or more elements selected from groups VIB, VIIB, VIII, and IVA;
   an inorganic oxide binder; and
   about 1 to about 5 wt % of a fluoride component.

2. The catalyst of claim 1, further comprising:
   a sulfur component.

3. The catalyst of claim 1, wherein the metal component comprises a metal selected from the group consisting of rhenium, nickel, cobalt, molybdenum, tungsten, tin, germanium, lead, indium, platinum, palladium, and combinations thereof.

4. The catalyst of claim 1, wherein the inorganic oxide binder comprises a material selected from the group consisting of alumina, silica, zirconia, titania, thoria, boria, magnesia, chromia, stannic oxide, and combinations thereof.

5. The catalyst of claim 1, wherein the acidic MFI molecular sieve has a Total Acidity of at least about 0.25.

6. The catalyst of claim 1, wherein the aluminosilicate zeolite component comprises mordenite.

7. The catalyst of claim 1, wherein the MFI molecular sieve comprises ZSM-5.

8. The catalyst of claim 1, wherein the catalyst comprises:
   about 20 wt. % to about 80 wt. % of the aluminosilicate zeolite component having the MOR framework type;
   about 10 wt. % to about 70 wt. % of the acidic MFI molecular sieve component;
   about 0.01 wt. % to about 10 wt. % of the metal component; and
   a balance of the inorganic oxide binder.

9. The catalyst of claim 1, wherein:
   the inorganic oxide binder comprises alumina; and
   the metal component comprises rhenium.

10. The catalyst of claim 1, wherein:
    the inorganic oxide binder comprises alumina; and
    the metal component comprises molybdenum.

* * * * *